United States Patent
Ingram et al.

(10) Patent No.: US 10,894,083 B2
(45) Date of Patent: Jan. 19, 2021

(54) STABLE AQUEOUS ANTI-VASCULAR ENDOTHELIAL GROWTH FACTOR (VEGF) ANTIBODY FORMULATION

(71) Applicant: Pfizer Inc., New York, NY (US)

(72) Inventors: Rebecca Lee Ingram, Billerica, MA (US); Sarah Elizabeth Weiser, Waltham, MA (US)

(73) Assignee: Pfizer Inc., New York, NY (US)

( * ) Notice: Subject to any disclaimer, the term of this patent is extended or adjusted under 35 U.S.C. 154(b) by 202 days.

(21) Appl. No.: 15/546,370

(22) PCT Filed: Jan. 20, 2016

(86) PCT No.: PCT/IB2016/050273
§ 371 (c)(1),
(2) Date: Jul. 26, 2017

(87) PCT Pub. No.: WO2016/120753
PCT Pub. Date: Aug. 4, 2016

(65) Prior Publication Data
US 2018/0000933 A1     Jan. 4, 2018

Related U.S. Application Data

(60) Provisional application No. 62/265,514, filed on Dec. 10, 2015, provisional application No. 62/108,811, filed on Jan. 28, 2015.

(51) Int. Cl.
*A61K 39/395*     (2006.01)
*C07K 16/22*     (2006.01)

(52) U.S. Cl.
CPC ........ *A61K 39/39591* (2013.01); *C07K 16/22* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 7,375,193 B2 | 5/2008 | Baca et al. | |
| 7,807,164 B2 | 10/2010 | Furfine et al. | |
| 8,110,546 B2 | 2/2012 | Dix et al. | |
| 8,142,776 B2 | 3/2012 | Liu et al. | |
| 8,372,396 B2 | 2/2013 | Andya et al. | |
| 8,420,081 B2 | 4/2013 | Fraunhofer et al. | |
| 8,921,527 B2 | 12/2014 | Mizushima et al. | |
| 9,226,961 B2 | 2/2016 | Gokarn et al. | |
| 2010/0316638 A1 | 12/2010 | Gurny et al. | |
| 2013/0017197 A1 | 1/2013 | Gurny et al. | |
| 2013/0028907 A1 | 1/2013 | Parshad et al. | |
| 2013/0216525 A1 | 8/2013 | Chen | |
| 2014/0004114 A1 | 1/2014 | Borras et al. | |
| 2014/0099301 A1* | 4/2014 | Gokarn | A61K 9/0019 424/133.1 |
| 2014/0314748 A1 | 10/2014 | Gokarn et al. | |
| 2015/0157709 A1 | 6/2015 | Everett et al. | |
| 2015/0182623 A1 | 7/2015 | Everett et al. | |
| 2015/0308988 A1 | 10/2015 | Babuka et al. | |
| 2015/0315270 A1 | 11/2015 | Baldi et al. | |
| 2016/0130337 A1 | 5/2016 | Gekkieva et al. | |
| 2016/0137727 A1 | 5/2016 | Le et al. | |
| 2016/0176986 A1 | 6/2016 | Armstrong et al. | |
| 2016/0297877 A1 | 10/2016 | Sigl | |
| 2016/0340420 A1 | 11/2016 | Zhang et al. | |
| 2017/0114127 A1 | 4/2017 | Trout et al. | |

FOREIGN PATENT DOCUMENTS

| | | |
|---|---|---|
| CN | 104906576 A | 9/2015 |
| CN | 106511997 A | 3/2017 |
| EP | 1650220 B1 | 9/2007 |
| EP | 2114456 B1 | 3/2015 |
| WO | 199856418 A1 | 12/1998 |
| WO | 2007124082 A2 | 11/2007 |
| WO | 2014160490 A1 | 10/2014 |
| WO | 2016103139 A1 | 6/2016 |

OTHER PUBLICATIONS

Krzystolik et al. (Arch Ophthalmol. 120: 338-346, 2002).*
Daugherty et al., "Formulation and Delivery Issues for Monoclonal Antibody Therapeutics", Advanced Drug Delivery Reviews, vol. 58, No. 5-6, pp. 686-706 (2006).
Wang et al., "Antibody Structure, Instability, and Formulation", Journal of Pharmaceutical Sciences, vol. 96, No. 1, pp. 1-26 (Jan. 2007).
Goswami, et al., "Developments and Challenges for mAb-Based Therapeutics", Antibodies, vol. 2, No. 3, pp. 452-500 (2013).
FDA Label for AVASTIN (bevacizumab), Reference ID: 4023368, most recent revision Dec. 2016, 40 pages.
"EPAR summary for the public" for AVASTIN, from the European Medicines Agency (May 2016), 4 pages.

* cited by examiner

*Primary Examiner* — Christine J Saoud
(74) *Attorney, Agent, or Firm* — Stephen E. Moyer

(57) ABSTRACT

The present invention relates to the field of pharmaceutical formulations of antibodies. Specifically, the present invention relates to a stable liquid antibody formulation and its pharmaceutical preparation and use. This invention is exemplified by an aqueous formulation of an anti-vascular endothelial growth factor (VEGF) antibody.

5 Claims, 3 Drawing Sheets
Specification includes a Sequence Listing.

SEQUENCE LISTING

```
<160> NUMBER OF SEQ ID NOS: 10

<210> SEQ ID NO 1
<211> LENGTH: 10
<212> TYPE: PRT
<213> ORGANISM: Mus musculus

<400> SEQUENCE: 1

Gly Tyr Thr Phe Thr Asn Tyr Gly Met Asn
1               5                   10

<210> SEQ ID NO 2
<211> LENGTH: 17
<212> TYPE: PRT
<213> ORGANISM: Mus musculus

<400> SEQUENCE: 2

Trp Ile Asn Thr Tyr Thr Gly Glu Pro Thr Tyr Ala Ala Asp Phe Lys
1               5                   10                  15

Arg

<210> SEQ ID NO 3
<211> LENGTH: 14
<212> TYPE: PRT
```

<213> ORGANISM: Mus musculus

<400> SEQUENCE: 3

Tyr Pro His Tyr Tyr Gly Ser Ser His Trp Tyr Phe Asp Val
1               5                   10

<210> SEQ ID NO 4
<211> LENGTH: 11
<212> TYPE: PRT
<213> ORGANISM: Mus musculus

<400> SEQUENCE: 4

Ser Ala Ser Gln Asp Ile Ser Asn Tyr Leu Asn
1               5                   10

<210> SEQ ID NO 5
<211> LENGTH: 7
<212> TYPE: PRT
<213> ORGANISM: Mus musculus

<400> SEQUENCE: 5

Phe Thr Ser Ser Leu His Ser
1               5

<210> SEQ ID NO 6
<211> LENGTH: 9
<212> TYPE: PRT
<213> ORGANISM: Mus musculus

<400> SEQUENCE: 6

Gln Gln Tyr Ser Thr Val Pro Trp Thr
1               5

<210> SEQ ID NO 7
<211> LENGTH: 123
<212> TYPE: PRT
<213> ORGANISM: Artificial Sequence
<220> FEATURE:
<223> OTHER INFORMATION: Humanized antibody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 8
<211> LENGTH: 108
<212> TYPE: PRT
<213> ORGANISM: Artificial Sequence

```
<220> FEATURE:
<223> OTHER INFORMATION: Humanized antibody sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Val Pro Trp
            85                  90                  95

Thr Phe Gly Gln Gly Thr Lys Val Glu Ile Lys Arg
        100                 105

<210> SEQ ID NO 9
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65              70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Lys Gly Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
```

```
225                 230                 235                 240
Gly Pro Ser Val Phe Leu Phe Pro Pro Lys Pro Asp Thr Leu Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Ile Ala Val Glu Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 10
<211> LENGTH: 212
<212> TYPE: PRT
<213> ORGANISM: Artificial Sequence
<220> FEATURE:
<223> OTHER INFORMATION: Humanized antibody sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Ser Gly Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
```

```
                        145                 150                 155                 160
            Val Thr Glu Gln Asp Ser Lys Asp Ser Thr Tyr Ser Leu Ser Ser Thr
                            165                 170                 175

Leu Thr Leu Ser Lys Ala Asp Tyr Glu Lys His Lys Val Tyr Ala Cys
                            180                 185                 190

Glu Val Thr His Gln Gly Leu Ser Ser Pro Val Thr Lys Ser Phe Asn
                            195                 200                 205

Arg Gly Glu Cys
                    210
```

STABLE AQUEOUS ANTI-VASCULAR ENDOTHELIAL GROWTH FACTOR (VEGF) ANTIBODY FORMULATION

FIELD OF THE INVENTION

The present invention relates to the field of pharmaceutical formulations of antibodies. Specifically, the present invention relates to a stable liquid antibody formulation and its pharmaceutical preparation and use.

BACKGROUND

Antibody preparations intended for therapeutic or prophylactic use require stabilizers to prevent loss of activity or structural integrity of the protein due to the effects of denaturation, oxidation or aggregation over a period of time during storage and transportation prior to use. These problems are exacerbated at the high concentrations of antibody often desired for therapeutic administration.

A major aim in the development of antibody formulations is to maintain antibody, solubility, stability and potency of its antigen binding. It is particularly desirable to avoid aggregates and particulates in solution which would require sterile filtration before use for intravenous or subcutaneous injection and limit route of administration. Formulation of antibody preparations requires careful selection of these factors among others to avoid denaturation of the protein and loss of antigen-binding activity. Accordingly, there is a need for a stable aqueous antibody formulation which stably supports high concentrations of bioactive antibody in solution and is suitable for parenteral administration, including intravenous, intraocular, intravitreal, intraarterial, intrathecal, intraventricular, intraurethral, intrasternal, intracranial, intramuscular, intra-ossial, intraperitoneal, intradermal or subcutaneous injection.

Furthermore there is a need to provide such a stable aqueous formulation for an anti-vascular endothelial cell growth factor (VEGF) antibody. It has been shown that the VEGF antibody is useful in the treatment of conditions or diseases that involve pathological angiogenesis, including tumors. There is a need for a stable aqueous antibody preparation of an anti-VEGF antibody to meet the medical need of patients suffering from cancer.

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literature and similar materials differs from or contradicts this application, including but not limited to defined terms, term usage, described techniques, or the like, this application controls.

SUMMARY OF THE INVENTION

Stable aqueous pharmaceutical formulations with an extended shelf life comprising an anti-vascular endothelial cell growth factor (VEGF) antibody are provided. It is demonstrated that the aqueous pharmaceutical formulation of the present invention with high antibody concentration is stable (e.g., having low levels of % HMMS (High Molecular Mass Species), % LMMS (Low Molecular Mass Species), % fragment, and oxidation) and suitable for parenteral administration.

In one aspect, provided is an aqueous formulation comprising: about 15 mg/ml to about 200 mg/ml of an anti-vascular endothelial cell growth factor (VEGF) antibody; a buffer; a polyol; a surfactant; a chelating agent; and wherein the formulation has a pH at about 5.0 to about 6.0.

In some embodiments, the buffer is a succinate buffer. In some embodiments, the buffer is a histidine buffer. In some embodiments, the concentration of the buffer is about 1 mM to about 40 mM.

In some embodiments, the polyol is sucrose. In some embodiments, the concentration of the polyol is about 1 mg/mL to about 150 mg/ml.

In some embodiments, the surfactant is a polysorbate, such as polysorbate 20 or 80. In some embodiments, the concentration of the surfactant is about 0.01 mg/ml to about 10 mg/ml.

In some embodiments, the chelating agent is EDTA (edetate). In some embodiments, the concentration of the chelating agent is about 0.01 mg/ml to about 1.0 mg/ml.

In some embodiments, the antibody comprises a heavy chain variable region (VH) complementary determining region one (CDR1) having the amino acid sequence shown in SEQ ID NO: 1, a VH CDR2 having the amino acid sequence shown in SEQ ID NO: 2, a VH CDR3 having the amino acid sequence shown in SEQ ID NO: 3, a light chain variable region (VL) CDR1 having the amino acid sequence shown in SEQ ID NO: 4, a VL CDR2 having the amino acid sequence shown in SEQ ID NO: 5, and a VL CDR3 having the amino acid sequence shown in SEQ ID NO: 6. In some embodiments, the antibody comprises a heavy chain variable region (VH) and a light chain variable region (VL), wherein the VH region comprises the amino acid sequence of SEQ ID NO: 7, and the VL region comprises the amino acid sequence of SEQ ID NO: 8. In some embodiments, the antibody is a human antibody, such as anti-VEGF antibody (AVASTIN® or rhuMAB VEGF). In some embodiments, the concentration of the antibody is about 15 mg/mL, about 20 mg/mL, about 25 mg/mL, about 30 mg/mL, about 35 mg/mL, about 40 mg/mL, about 45 mg/ml, about 50 mg/mL, about 55 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, or about 160 mg/mL.

In another aspect, provided is a aqueous formulation comprising: about 25 mg/ml of an anti-vascular endothelial growth factor (VEGF) protein; about 20 mM succinate or histidine buffer; about 85 mg/mL sucrose; about 0.2 mg/ml polysorbate 80; about 0.05 mg/ml EDTA; wherein the antibody comprises a heavy chain variable region comprising the amino acid sequence of SEQ ID NO: 7, and a light chain variable region comprising the amino acid sequence of SEQ ID NO: 8; and wherein the formulation has pH at about 5.5 or 5.8. In some embodiments, the antibody is anti-VEGF antibody (AVASTIN® or rhuMAB VEGF).

In another aspect, provided is a method for treating or inhibiting cancer in a subject in need thereof, comprising administering to the subject a therapeutically effective amount of the formulation as described herein. In some embodiments, the formulation is administered to the subject subcutaneously or intravenously.

In another aspect, provided is a use of the formulation as described herein for the manufacture of a medicament for treatment of cancer in a subject.

In some embodiments, the cancer is selected from the group consisting of rhe colorectal cancer, rectal cancer, non-squamous non-small cell lung cancer (NSCLC), non-Hodgkins lymphoma (NHL), metastatic renal cell cancer (mRCC), prostate cancer, liver cancer, pancreatic cancer, soft-tissue sarcoma, kaposi's sarcoma, carcinoid carcinoma, head and neck cancer, melanoma, ovarian cancer, mesothelioma, glioblastoma, cervical cancer, breast cancer, and multiple myeloma.

In some embodiments, the formulation as described herein has a shelf life of at least about 36 months.

DETAILED DESCRIPTION

Figure 1:
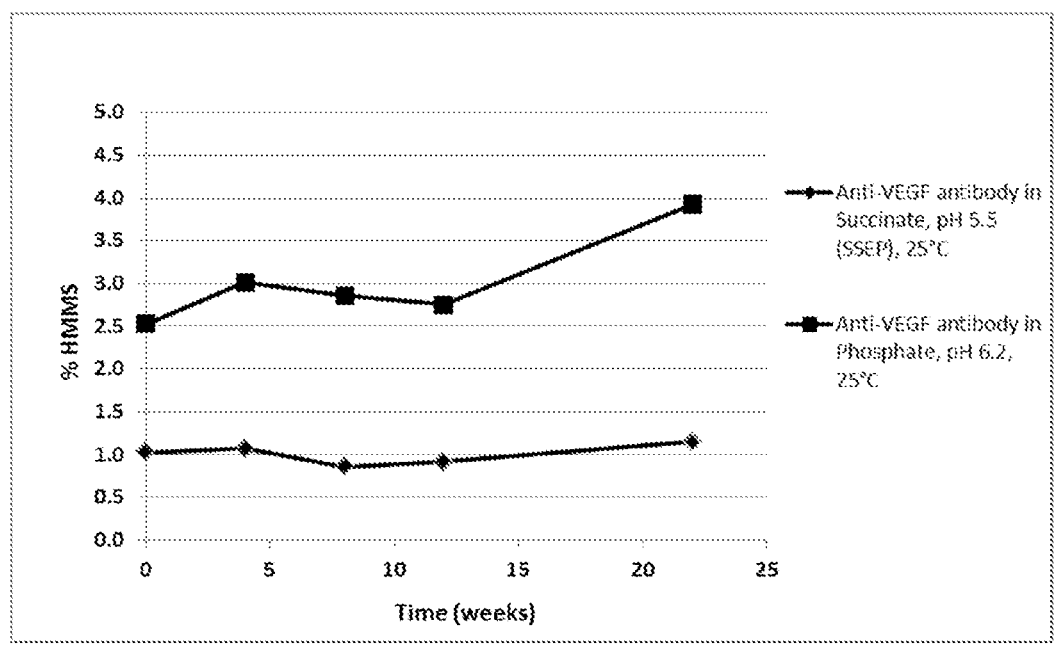
FIG. 1 depicts a graph summarizing the amount of high molecular mass species (% HMMS) by SE-HPLC (Size Exclusion-High Performance Liquid Chromatography) for anti-VEGF antibody in SSEP or Commercial formulation (Phosphate) at 25° C.

Disclosed herein are stable aqueous pharmaceutical formulations with an extended shelf-life comprising an anti-vascular endothelial growth factor (VEGF) antibody. It is demonstrated that the aqueous pharmaceutical formulation of the present invention stably supports high concentration of antibody (e.g., having low levels of % HMMS (High Molecular Mass Species) at an antibody concentration of at least about 15 mg/mL) and is suitable for parenteral administration, including subcutaneous, intravenous, intramuscular, intraperitoneal, or intradermal injection. Accordingly, in one aspect, provided is an aqueous formulation comprising: about 15 mg/ml to about 200 mg/ml of an anti-vascular endothelial growth factor (VEGF) antibody, or antigen-binding fragment thereof; a buffer; a polyol; a surfactant; a chelating agent; and wherein the formulation has a pH at about 5.0 to about 6.0. For example, in some embodiments, provided is an aqueous formulation comprising: about 15 mg/ml to about 200 mg/ml of an anti-vascular endothelial growth factor (VEGF) antibody (e.g., anti-VEGF antibody); about 1 mM to about 40 mM of a buffer (e.g., succinate buffer); about 1 mg/mL to about 300 mg/mL of a polyol (e.g., sucrose); about 0.01 mg/ml to about 10 mg/ml of a surfactant (e.g., polysorbate 80); about 0.01 mg/ml to about 1.0 mg/ml of a chelating agent (e.g., EDTA (or edetate)); wherein the formulation has a pH at about 5.0 to about 6.0. In some embodiments, the antibody concentration is about 22.5 mg/mL to about 27.5 mg/mL. In other embodiments, the antibody concentration is about 100 to about 150 mg/mL.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The following terms, unless otherwise indicated, shall be understood to have the following meanings: the term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the term "formulation" as it relates to an antibody is meant to describe the antibody in combination with a pharmaceutically acceptable excipient comprising at least one buffer, at least one surfactant, at least one chelating agent, and wherein the pH is as defined.

The terms "pharmaceutical composition" or "pharmaceutical formulation" refer to preparations which are in such form as to permit the biological activity of the active ingredients to be effective.

"Pharmaceutically acceptable excipients" (vehicles, additives) are those, which can safely be administered to a subject to provide an effective dose of the active ingredient employed. The term "excipient" or "carrier" as used herein refers to an inert substance, which is commonly used as a diluent, vehicle, preservative, binder or stabilizing agent for drugs. As used herein, the term "diluent" refers to a pharmaceutically acceptable (safe and non-toxic for administration to a human) solvent and is useful for the preparation of the aqueous formulations herein. Exemplary diluents include, but are not limited to, sterile water and bacteriostatic water for injection (BWFI).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')2, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

As used herein, the term "human antibody" is intended to include antibodies having variable and constant regions derived from human germline immunoglobulin sequences. This definition of a human antibody includes antibodies comprising at least one human heavy chain polypeptide or at least one human light chain polypeptide. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J Immunol. 138: 4534-4538 (1987), and Brown et al. Cancer Res. 47: 3577-3583 (1987). Other references describe rodent CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986). Another reference describes rodent CDRs supported by recombinantly veneered rodent framework regions. See, for example, European Patent Publication No. 0519596. These"humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160.

As used herein, the term "recombinant antibody" is intended to include all antibodies that are prepared, expressed, created or isolated by recombinant means, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes or antibodies prepared, such recombinant human antibodies can be subjected to in vitro mutagenesis.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to VEGF, e.g., the antibodies compete for binding to the antigen.

As used herein, the terms "isolated antibody" or "purified antibody" refers to an antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature.

The term "antagonist antibody" refers to an antibody that binds to a target and prevents or reduces the biological effect of that target. In some embodiments, the term can denote an antibody that prevents the target, e.g., VEGF, to which it is bound from performing a biological function.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a VEGF epitope is an antibody that binds this epitope sequence with greater affinity, avidity, more readily, and/or with greater duration than it binds to other sequences. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, the term "human VEGF" refers to the 165-amino acid vascular endothelial cell growth factor and related 121-, 189-, and 206-amino acid vascular endothelial cell growth factors, as described by Leung et al. *Science*, 246:1306 (1989), and Houck et al. *Mol. Endocrin.*, 5:1806 (1991), together with the naturally occurring allelic and processed forms thereof. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "therapeutically effective amount" refers to an amount effective, at dosages and for periods of time necessary, to achieve the desired therapeutic result, which in the context of anti-VEGF antibodies includes treatment or prophylactic prevention of the targeted pathologic condition for example cancer. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Likewise, a therapeutically effective amount of the antibody or antibody portion may vary according to factors such as the disease state, age, sex, and weight of the individual, the ability of the antibody or antibody portion to elicit a desired response in the individual, and the desired route of administration of the antibody formulation. A therapeutically effective amount is also one in which any toxic or detrimental effects of the antibody or antibody portion are outweighed by the therapeutically beneficial effects.

As used herein, the term "treatment" refers to both therapeutic treatment and prophylactic or preventative measures, wherein the object is to prevent or slow down (lessen) the targeted pathologic condition (e.g., any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.). Those in need of treatment include those already with the condition as well as those prone to have the condition or those in whom the condition is to be prevented. As used herein, "treatment" is an approach for obtaining beneficial or desired clinical results including, but not limited to, one or more of the following: including lessening severity, alleviation of one or more symptoms associated with the pathologic condition.

An "effective amount" of drug, formulation, compound, or pharmaceutical composition is an amount sufficient to effect beneficial or desired results including clinical results such as alleviation or reduction of the targeted pathologic condition. An effective amount can be administered in one or more administrations. For purposes of this invention, an effective amount of drug, compound, or pharmaceutical composition is an amount sufficient to treat, ameliorate, or reduce the intensity of the targeted pathologic condition. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, the term "subject" for purposes of treatment includes any subject, and preferably is a subject who is in need of the treatment of the targeted pathologic condition (e.g., cancer). For purposes of prevention, the subject is any subject, and preferably is a subject that is at risk for, or is predisposed to, developing the targeted pathologic condition. The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "polynucleotide" or "nucleic acid", used interchangeably herein, means a polymeric form of nucleotides either ribonucleotides or deoxynucleotides or a modified form of either type of nucleotide and may be single and double stranded forms. A "polynucleotide" or a "nucleic acid" sequence encompasses its complement unless otherwise specified. As used herein, the term "isolated polynucleotide" or "isolated nucleic acid" means a polynucleotide of genomic, cDNA, or synthetic origin or some combination thereof, which by virtue of its origin or source of derivation, the isolated polynucleotide has one to three of the following: (1) is not associated with all or a portion of a polynucleotide with which the "isolated polynucleotide" is found in nature, (2) is operably linked to a polynucleotide to which it is not linked in nature, or (3) does not occur in nature as part of a larger sequence.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline, normal (0.9%) saline, or 5% dextrose. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$K_{off}$", as used herein, is intended to refer to the off rate constant for dissociation of an antibody from the antibody/antigen complex.

The term "$K_d$", as used herein, is intended to refer to the dissociation constant of an antibody-antigen interaction. One way of determining the Kd or binding affinity of antibodies to human VEGF is by measuring binding affinity of monofunctional Fab fragments of the antibody. To obtain monofunctional Fab fragments, an antibody (for example, IgG) can be cleaved with papain or expressed recombinantly. The affinity of an anti-VEGF Fab fragment of an antibody can be determined by surface plasmon resonance (BIAcorC1GM000™ surface plasmon resonance (SPR) system, BIAcore, INC, Piscaway N.J.). CM5 chips can be activated with N-ethyl-N'-(3-dimethylaminopropyl)-carbodiinide hydrochloride (EDC) and N-hydroxysuccinimide (NHS) according to the supplier's instructions.

"Reducing incidence" means any of reducing severity (which can include reducing need for and/or amount of (e.g., exposure to) other drugs and/or therapies generally used for this condition. As is understood by those skilled in the art, individuals may vary in terms of their response to treatment, and, as such, for example, a "method of reducing incidence" reflects administering the human VEGF antagonist antibody based on a reasonable expectation that such administration may likely cause such a reduction in incidence in that particular individual.

"Ameliorating" means a lessening or improvement of one or more symptoms as compared to not administering a VEGF antagonist antibody. "Ameliorating" also includes shortening or reduction in duration of a symptom.

Reference to "about" a value or parameter herein includes (and describes) embodiments that are directed to that value or parameter per se. For example, description referring to "about X" includes description of "X." Numeric ranges are inclusive of the numbers defining the range.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

When introducing elements of the present invention or the preferred embodiment(s) thereof, the articles "a", "an", "the" and "said" are intended to mean that there are one or more of the elements. The terms "comprising", "comprise", "comprises", "including" and "having" are intended to be inclusive and mean that there may be additional elements other than the listed elements. It is understood that wherever embodiments are described herein with the language "comprising," otherwise analogous embodiments described in terms of "consisting of" and/or "consisting essentially of" are also provided.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

Anti-VEGF Antibody Formulation

In one aspect, provided is a stable aqueous formulation comprising: about 15 mg/ml to about 200 mg/ml of an anti-vascular endothelial growth factor (VEGF) antibody, or antigen-binding fragment thereof; a buffer; a polyol; a surfactant; a chelating agent; and wherein the formulation has a pH at about 5.0 to about 6.0. The formulation described herein have an extended shelf life, preferably of at least or more than about 36 months (e.g., at about 5° C.).

In some embodiments, the formulation comprises at least one anti-VEGF antibody. For example, the anti-VEGF antibody is a human antibody (e.g., AVASTIN® or rhuMAB VEGF). In some embodiments, more than one antibody may be present. At least one, at least two, at least three, at least four, at least five, or more, different antibodies can be present. Generally, the two or more different antibodies have complementary activities that do not adversely affect each other. The, or each, antibody can also be used in conjunction with other agents that serve to enhance and/or complement the effectiveness of the antibodies.

In some embodiments, the anti-VEGF antibody in the formulation of the present invention is an antibody that dissociates from human VEGF with a $K_d$ of $1\times10^{-8}$ M or less and a $K_{off}$ rate constant of $1\times10^{-3}$ $s^{-1}$ or less, both determined by surface plasmon resonance, and neutralizes human VEGF cytotoxicity in a standard in vitro L929 assay with an $IC_{50}$ of $1\times10^{-7}$ M or less. In some embodiments, the anti-VEGF antibody in the formulation of the present invention is an antibody that dissociates from human VEGF with a $K_{off}$ rate constant of $5\times10^{-4}$ $s^{-1}$ or less, or $K_{off}$ rate constant of $1\times10^{-4}$ $s^{-1}$ or less. In some embodiments, the anti-VEGF antibody in the formulation of the present invention is an antibody neutralizes human VEGF cytotoxicity in a standard in vitro L929 assay with an $IC_{50}$ of $1\times10^{-7}$ M or less, an $IC_{50}$ of $1\times10^{-8}$ M or less, an $IC_{50}$ of $1\times10^{-9}$ M or less, or an $IC_{50}$ of $1\times10^{-10}$ M or less. In some embodiment, the anti-VEGF antibody in the formulation of the present invention also neutralizes VEGF-induced cellular activation, as assessed using a standard in vitro assay for VEGF-induced ELAM-1 expression on human umbilical vein endothelial cells (HU-VEC). See, e.g., U.S. Pat. Nos. 6,090,382, 6,258,562, and 8,216,583, each incorporated by reference herein.

In some embodiments, the anti-VEGF antibody in the formulation of the present invention comprises a heavy chain variable region (VH) complementary determining region one (CDR1) having the amino acid sequence shown in SEQ ID NO: 1, a VH CDR2 having the amino acid sequence shown in SEQ ID NO: 2, a VH CDR3 having the amino acid sequence shown in SEQ ID NO: 3, or a variant of SEQ ID NO: 3, a light chain variable region (VL) CDR1 having the amino acid sequence shown in SEQ ID NO: 4, a VL CDR2 having the amino acid sequence shown in SEQ ID NO: 5, and a VL CDR3 having the amino acid sequence shown in SEQ ID NO: 6.

TABLE 1

| SEQ ID NO: | Sequence | Description |
|---|---|---|
| 1 | GYTFTNYGMN | AVASTIN ® VH CDR1 |
| 2 | WINTYTGEPTYAADFKR | AVASTIN ® VH CDR2 |
| 3 | YPHYYGSSHWYFDV | AVASTIN ® VH CDR3 |
| 4 | SASQDISNYLN | AVASTIN ® VL CDR1 |
| 5 | FTSSLHS | AVASTIN ® VL CDR2 |
| 6 | QQYSTVPWT | AVASTIN ® VL CDR3 |
| 7 | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSS | AVASTIN ® VH |
| 8 | DIQMTQSPSSLSASVGDRVTITCSASQDISNYLNWY QQKPGKAPKVLIYFTSSLHSGVPSRFSGSGSGTDFT LTISSLQPEDFATYYCQQYSTVPWTFGQGTKVEIKR | AVASTIN ® VL |

TABLE 1-continued

| SEQ ID NO: | Sequence | Description |
|---|---|---|
| 9 | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASKGSVFPLAPSSKSTS GGTAALGCLVKDYFPEPVTVSWNSGALTSGVHTFP AVLQSSGLYSLSSVVTVPSSSLGTQTYICNVNHKPS NTKVDKKVEPKSCDKTHTCPPCPAPELLGGPSVFLF PPKPDTLISRTPEVTCVVVDVSHEDPEVKFNWYVDG VEVHNAKTKPREEQYNSTYRVVSVLTVLHQDWLNG KEYKCKVSNKALPAPIEKTISKAKGQPREPQVYTLPP SREEMTKNQVSLTCLVKGFYPSIAVEESNGQPENNY KTTPPVLDSDGSFFLYSKLTVDKSRWQQGNVFSCS VMHEALHNHYTQKSLSLSPGK | AVASTIN ® heavy chain |
| 10 | DIQMTQSPSSLSASVGDRVTITCSASQDSNYLNWY QQKPGKAPKVLIYFTSSLHSGVPSRFSGSGSGTDFT LTISSLQPEDFATYYCQQYSTVPWTFGQGTKVEIKR TVAAPSVFIFPPSDEQLSGASVVCLLNNFYPREAKV QWKVDNALQSGNSQESVTEQDSKDSTYSLSSTLTL SKADYEKHKVYACEVTHQGLSSPVTKSFNRGEC | AVASTIN ® light chain |

In some embodiments, the anti-VEGF antibody in the formulation of the present invention, comprises a heavy chain variable region (VH) and a light chain variable region (VL), wherein the VH region comprises the amino acid sequence of SEQ ID NO: 7, and the VL region comprises the amino acid sequence of SEQ ID NO: 8. In some embodiments, the anti-VEGF antibody in the formulation of the present invention, has an IgG1 heavy chain constant region or an IgG4 heavy chain constant region, or is a Fab fragment or a single chain Fv fragment.

In some embodiment, the anti-VEGF antibody in the formulation of the present invention is AVASTIN® (anti-VEGF antibody or rhuMAb VEGF).

The antibody may be present in the formulation at a concentration ranging from about 0.1 mg/ml to about 200 mg/ml, from about 15 mg/ml to 200 mg/ml, from about 20 mg/ml to about 175 mg/ml, or from about 25 mg/ml to about 150 mg/ml. For example, in some embodiments, the concentration of antibody is about 0.5 mg/ml, about 1 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 70 mg/ml, about 80 mg/ml, about 90 mg/ml, about 100 mg/ml, about 101 mg/ml, about 102 mg/ml, about 102.5 mg/ml, about 103 mg/ml, about 103.5 mg/ml, about 104 mg/ml, about 104.5 mg/ml, about 105 mg/ml, about 105.5 mg/ml, about 106 mg/ml, about 106.5 mg/ml, about 107 mg/ml, about 107.5 mg/ml, about 108 mg/ml, about 108.5 mg/ml, about 109 mg/ml, about 109.5 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 133 mg/ml, about 134 mg/ml, about 135 mg/ml, about 136 mg/ml, about 137 mg/ml, about 138 mg/ml, about 139 mg/ml, about 140 mg/ml, about 141 mg/ml, about 142 mg/ml, about 143 mg/ml, about 144 mg/ml, about 145 mg/ml, about 146 mg/ml, about 147 mg/ml, about 148 mg/ml, about 149 mg/ml, about 150 mg/ml, about 151 mg/ml, about 152 mg/ml, about 153 mg/ml, about 154 mg/ml, about 155 mg/ml, about 156 mg/ml, about 157 mg/ml, about 158 mg/ml, about 159 mg/ml, about 160 mg/ml, about 170 mg/ml, about 180 mg/ml, about 190 mg/ml, or about 200 mg/ml.

According to the present invention, the buffer (e.g., succinate buffer) provides the formulation with a pH close to physiological pH for reduced risk of pain or anaphylactoid side effects on injection and also provides enhanced antibody stability and resistance to aggregation, oxidation, and fragmentation.

The buffer can be, for example without limitation, acetate, succinate (e.g., disodium succinate hexahydrate), gluconate, citrate, histidine, acetic acid, phosphate, phosphoric acid, ascorbate, tartaric acid, maleic acid, glycine, lactate, lactic acid, ascorbic acid, imidazole, bicarbonate and carbonic acid, succinic acid, sodium benzoate, benzoic acid, gluconate, edetate, acetate, malate, imidazole, tris, phosphate, and mixtures thereof. Preferably the buffer is succinate, wherein the succinate can comprise a disodium succinate hexahydrate (basic form) and/or succinic acid or a mixture thereof.

The concentration of the buffer can range from about 0.1 millimolar (mM) to about 100 mM. Preferably, the concentration of the buffer is from about 0.5 mM to about 50 mM, further preferably about 1 mM to about 30 mM, more preferably about 1 mM to about 25 mM. Preferably, the concentration of the buffer is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. In some embodiment, the buffer is a succinate buffer in the concentration of about 20 mM.

The concentration of the buffer can also range from about 0.01 mg/ml to about 30 mg/ml, from about 0.1 mg/ml to about 5 mg/ml, or from about 0.5 mg/ml to about 4 mg/ml. For example, the concentration of the buffer is about 0.01 mg/ml, 0.02 mg/ml, 0.03 mg/ml, about 0.04 mg/ml, about 0.05 mg/ml, about 0.06 mg/ml, about 0.07 mg/ml, 0.08 mg/ml, 0.09 mg/ml, about 0.10 mg/ml, 0.11 mg/ml, 0.12 mg/ml, 0.13 mg/ml, about 0.14 mg/ml, about 0.15 mg/ml, about 0.16 mg/ml, about 0.17 mg/ml, 0.18 mg/ml, 0.19 mg/ml about 0.20 mg/ml, about 0.25 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 2.0 mg/ml, about 3.0 mg/ml, about 4.0 mg/ml, about 5.0 mg/ml, about 6.0 mg/ml, about 7.0 mg/ml, about 8.0 mg/ml, about 9.0 mg/ml, about 10.0 mg/ml, about 11.0 mg/ml, about 12.0 mg/ml, about 13.0 mg/ml, about 14.0 mg/ml, about 15.0 mg/ml, about 16.0 mg/ml, about 17.0 mg/ml, about 18.0 mg/ml, about 19.0 mg/ml, about 20 mg/ml, about 21.0 mg/ml, about 22.0 mg/ml, about 23.0 mg/ml, about 24.0 mg/ml, about 25.0 mg/ml, about 26.0 mg/ml, about 27.0 mg/ml, about 28.0 mg/ml, about 29.0 mg/ml, or about 30 mg/ml. In some embodiments, the buffer is a succinate buffer comprising about 0.5-5.0 mg/mL disodium succinate hexahydrate and about 0.1-1.0 mg/mL succinic acid. In some embodiments the buffer is a succinate buffer comprising about 4.08 mg/mL disodium succinate hexahydrate and about 0.58 mg/mL succinic acid. In some embodiments the buffer is a succinate buffer comprising about 2.362 mg/mL succinic acid.

In some embodiments, the polyol can have a molecular weight that, for example without limitation, is less than about 600 kD (e.g., in the range from about 120 to about 400 kD), and comprises multiple hydroxyl groups including sugars (e.g., reducing and nonreducing sugars or mixtures thereof, saccharide, or a carbohydrate), sugar alcohols, sugar acids, or a salt or mixtures thereof. Examples of non-reducing sugar, include, but are not limited to, sucrose, trehalose, and mixtures thereof. In some embodiments, the polyol is mannitol, trehalose, sorbitol, erythritol, isomalt, lactitol, maltitol, xylitol, glycerol, lactitol, propylene glycol, polyethylene glycol, inositol, or mixtures thereof. In other embodiments, the polyol can be, for example without limitation, a monosaccharide, disaccharide or polysaccharide, or mixtures of any of the foregoing. The saccharide or carbohydrate can be, for example without limitation, fructose, glucose, mannose, sucrose, sorbose, xylose, lactose, maltose, sucrose, dextran, pullulan, dextrin, cyclodextrins, soluble starch, hydroxyethyl starch, water-soluble glucans, or mixtures thereof.

The concentration of the polyol in the formulation ranges from about 1 mg/ml to about 300 mg/ml, from about 1 mg/ml to about 200 mg/ml, or from about 1 mg/ml to about 120 mg/ml. Preferably the concentration of the polyol in the formulation is about 50 mg/ml to about 120 mg/ml, from about 60 mg/ml to about 110 mg/ml, or from about 80 mg/ml to about 90 mg/ml). For example, the concentration of the polyol in the formulation is about 0.5 mg/ml, about 1 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 65 mg/ml, about 70 mg/ml, about 75 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 133 mg/ml, about 134 mg/ml, about 135 mg/ml, about 136 mg/ml, about 137 mg/ml, about 138 mg/ml, about 139 mg/ml, about 140 mg/ml, about 141 mg/ml, about 142 mg/ml, about 143 mg/ml, about 144 mg/ml, about 145 mg/ml, about 146 mg/ml, about 147 mg/ml, about 148 mg/ml, about 149 mg/ml, or about 150 mg/ml.

In some embodiments, the polyol is sucrose at a concentration of from about 1 mg/ml to about 300 mg/ml, from about 1 mg/ml to about 200 mg/ml, or from about 1 mg/ml to about 120 mg/ml. Preferably the concentration of the sucrose in the formulation is about 50 mg/ml to about 120 mg/ml, from about 60 mg/ml to about 110 mg/ml, or from about 80 mg/ml to about 90 mg/ml. In some embodiments, the concentration of sucrose in the formulation is about 85 mg/ml.

Surfactants, as used in the present invention, can alter the surface tension of a liquid antibody formulation. In certain embodiments, the surfactant reduces the surface tension of a liquid antibody formulation. In still other embodiments, the surfactant can contribute to an improvement in stability of any of the antibody in the formulation. The surfactant can also reduce aggregation of the formulated antibody (e.g., during shipping and storage) and/or minimize the formation of particulates in the formulation and/or reduces adsorption (e.g., adsorption to a container). For example, the surfactant can also improve stability of the antibody during and after a freeze/thaw cycle. The surfactant can be, for example without limitation, a polysorbate, poloxamer, triton, sodium dodecyl sulfate, sodium laurel sulfate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl PEG 5 linoleammonium chloride, polyethylene glycol, polypropylene glycol, and mixtures thereof. The surfactant can be, for example without limitation, polysorbate 20, polysorbate 21, polysorbate 40, polysorbate 60, polysorbate 61, polysorbate 65, polysorbate 80, polysorbate 81, polysorbate 85, PEG3350 and mixtures thereof.

The concentration of the surfactant generally ranges from about 0.01 mg/ml to about 10 mg/ml, from about 0.01 mg/ml to about 5.0 mg/ml, from about 0.01 mg/ml to about 2.0 mg/ml, from about 0.01 mg/ml to about 1.5 mg/ml, from about 0.01 mg/ml to about 1.0 mg/ml, from about 0.01 mg/ml to about 0.5 mg/ml, from about 0.01 mg/ml to about 0.4 mg/ml, from about 0.01 mg/ml to about 0.3 mg/ml, from about 0.01 mg/ml to about 0.2 mg/ml, from about 0.01 mg/ml to about 0.15 mg/ml, from about 0.01 mg/ml to about 0.1 mg/ml, from about 0.01 mg/ml to about 0.05 mg/ml, from about 0.1 mg/ml to about 1 mg/ml, from about 0.1 mg/ml to about 0.5 mg/ml, or from about 0.1 mg/ml to about 0.3 mg/ml. Further preferably the concentration of the surfactant is about 0.05 mg/ml, about 0.06 mg/ml, about 0.07 mg/ml, about 0.08 mg/ml, about 0.09 mg/ml, about 0.1 mg/ml, about 0.15 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, or about 1 mg/ml.

In some embodiments, the polysorbate is polysorbate 80 at a concentration ranging from about 0.1 mg/ml to about 0.3 mg/ml, for example, at 0.2 mg/ml.

Chelating agents, as used in the present invention, lower the formation of reduced oxygen species, reduce acidic species (e.g., deamidation) formation, reduce antibody aggregation, and/or reduce antibody fragmentation, and/or reduce antibody oxidation in the formulation of the present invention. For example, the chelating agent can be a multidentate ligand that forms at least one bond (e.g., covalent, ionic, or otherwise) to a metal ion and acts as a stabilizer to complex with species, which might otherwise promote instability.

In some embodiments, the chelating agent can be selected from the group consisting of aminopolycarboxylic acids, hydroxyaminocarboxylic acids, N-substituted glycines, 2-(2-amino-2-oxocthyl) aminoethane sulfonic acid (BES), deferoxamine (DEF), citric acid, niacinamide, and desoxycholates and mixtures thereof. In some embodiments, the chelating agent is selected from the group consisting of ethylenediaminetetraacetic acid (EDTA), diethylenetriamine pentaacetic acid 5 (DTPA), nitrilotriacetic acid (NTA), N-2-acetamido-2-iminodiacetic acid (ADA), bis(aminoethyl) glycolether, N,N,N',N'-tetraacetic acid (EGTA), trans-diaminocyclohexane tetraacetic acid (DCTA), glutamic acid, and aspartic acid, N-hydroxyethyliminodiacetic acid (HIMDA), N,N-bis-hydroxyethylglycine (bicine) and N-(trishydroxymethylmethyl) 10 glycine (tricine), glycylglycine, sodium desoxycholate, ethylenediamine, propylenediamine, diethylenetriamine, triethylenetetraamine (trien), disodium edetate dihydrate (or disodium EDTA dihydrate or EDTA disodium salt), calcium EDTA oxalic acid, malate, citric acid, citric acid monohydrate, and trisodium citrate-dihydrate, 8-hydroxyquinolate, amino acids, histidine, cysteine, methionine, peptides, polypeptides, and proteins and mixtures thereof. In some embodiments, the chelating agent is selected from the group consisting of salts of EDTA including dipotassium edetate, disodium edetate, edetate calcium disodium, sodium edetate, trisodium edetate, and potassium edetate; and a suitable salt of deferoxamine (DEF) is deferoxamine mesylate (DFM), or mixtures thereof. Chelating agents used in the invention can be present, where possible, as the free acid or free base form or salt form of the compound, also as an anhydrous, solvated or hydrated form of the compound or corresponding salt.

In a preferred embodiment the chelating agent is EDTA (edetate).

The concentration of the chelating agent generally ranges from about 0.01 mg/ml to about 50 mg/ml, from about 0.1 mg/ml to about 10.0 mg/ml, from about 5 mg/ml to about 15.0 mg/ml, from about 0.01 mg/ml to about 1.0 mg/ml, from about 0.02 mg/ml to about 0.5 mg/ml, from about 0.025 mg/ml to about 0.075 mg/ml. Further preferably, the concentration of the chelating agent generally ranges from about 0.01 mM to about 2.0 mM, from about 0.01 mM to about 1.5 mM, from about 0.01 mM to about 0.5 mM, from about 0.01 mM to about 0.4 mM, from about 0.01 mM to about 0.3 mM, from about 0.01 mM to about 0.2 mM, from about 0.01 mM to about 0.15 mM, from about 0.01 mM to about 0.1 mM, from about 0.01 mM to about 0.09 mM, from about 0.01 mM to about 0.08 mM, from about 0.01 mM to about 0.07 mM, from about 0.01 mM to about 0.06 mM, from about 0.01 mM to about 0.05 mM, from about 0.01 mM to about 0.04 mM, from about 0.01 mM to about 0.03 mM, from about 0.01 mM to about 0.02 mM, from about 0.02, or from about 0.05 mM to about 0.01 mM. Preferably the concentration of the chelating agent can be about 0.01 mg/ml, about 0.02 mg/ml, about 0.025 mg/ml, about 0.03 mg/ml, about 0.04 mg/ml, about 0.05 mg/ml, about 0.06 mg/ml, about 0.07 mg/ml, about 0.075 mg/ml, about 0.08 mg/ml, about 0.09 mg/ml, about 0.10 mg/ml, or about 0.20 mg/ml. Further preferably the concentration of chelating agent is about 0.025 mg/ml, about 0.03 mg/ml, about 0.035 mg/ml, about 0.04 mg/ml, about 0.045 mg/ml, about 0.05 mg/ml, about 0.055 mg/ml, about 0.06 mg/ml, about 0.065 mg/ml, about 0.07 mg/ml, or about 0.075 mg/ml. Most preferably, the concentration of the chelating agent is about 0.05 mg/ml.

According to some embodiments of the present invention, the pH can be in the range of about pH 5.0 to about 6.6, preferably between about pH 5.0 to 6.5 or about 5.0 to 6.0, and most preferably between pH 5.2 to 5.8. For example, the anti-VEGF antibody in the formulation of the present invention at the pH range of 5.2 to 5.8 had less formation of high molecular mass species compared to at pH 5.0 or pH 6.5. Accordingly, in some embodiments, the pH for the formulation of the present invention can be in the range selected from between any one of about pH 5.2, 5.3, 5.4, 5.5, or 5.6 and any one of about pH 6.5, 6.4, 6.3, 6.2, 6.1, 6.0, 5.9, 5.8 or 5.7. In some embodiments the pH can be selected from pH values of any of about pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4 or 7.5. Preferably, the pH is pH 5.5+/−0.5, and most preferably, the pH is pH 5.5+/−0.3.

In some embodiments the formulation can comprise a preservative. Preferably the preservative agent is selected from phenol, m-cresol, benzyl alcohol, benzalkonium chloride, benzalthonium chloride, phenoxyethanol and methyl paraben.

The concentration of the preservative generally ranges from about 0.001 mg/ml to about 50 mg/ml, from about 0.005 mg/ml to about 15.0 mg/ml, from about 0.008 mg/ml to about 12.0 mg/ml or from about 0.01 mg/ml to about 10.0 mg/ml. Preferably the concentration of preservative can be about 0.1 mg/ml, 0.2 mg/ml, 0.3 mg/ml, about 0.4 mg/ml, about 0.5 mg/ml, about 0.6 mg/ml, about 0.7 mg/ml, 0.8 mg/ml, 0.9 mg/ml about 1.0 mg/ml, 2.0 mg/ml, 3.0 mg/ml, about 4.0 mg/ml, about 5.0 mg/ml, about 6.0 mg/ml, about 7.0 mg/ml, 8.0 mg/ml, 9.0 mg/ml about 9.1 mg/ml, about 9.2 mg/ml, 9.3 mg/ml, 9.4 mg/ml, 9.5 mg/ml, 9.6 mg/ml, 9.7 mg/ml, 9.8 mg/ml, 9.9 mg/ml, 10.0 mg/ml. Most preferably, the concentration of preservative is about 0.1 mg/ml or 9.0 mg/mL.

In some embodiments, the formulation does not contain a preservative.

In some embodiments, the antibody can be selected from the group consisting of monoclonal antibodies, polyclonal antibodies, antibody fragments (e.g., Fab, Fab', F(ab')2, Fv, Fc, ScFv etc.), chimeric antibodies, bispecific antibodies, heteroconjugate antibodies, single chain (ScFv), mutants thereof, fusion proteins comprising an antibody portion (e.g., a domain antibody), humanized antibodies, human antibodies, and any other modified configuration of the immunoglobulin molecule that comprises an antigen recognition site of the required specificity, including glycosylation variants of antibodies, amino acid sequence variants of antibodies, and covalently modified antibodies. The antibody may be murine, rat, human, or any other origin (including chimeric or humanized antibodies). In some embodiments, the antibody can be human but is more preferably humanized. Preferably the antibody is isolated, further preferably it is substantially pure. Where the antibody is an antibody fragment this preferably retains the functional characteristics of the original antibody i.e. the ligand binding and/or antagonist or agonist activity.

In some embodiments, the antibody heavy chain constant region may be from any type of constant region, such as IgG, IgM, IgD, IgA, and IgE; and any isotypes, such as IgG1, IgG2, IgG3, and IgG4. Preferably the antibody is an IgG1 antibody.

According to a further aspect of the present invention there is provided an aqueous formulation comprising or consisting of: about 15 mg/ml to about 200 mg/ml of an anti-vascular endothelial growth factor (VEGF) antibody, or an antigen-binding fragment thereof; about 1 mM to about 100 mM of a buffer; about 1 mg/mL to about 300 mg/mL of a polyol; about 0.01 mg/ml to about 10 mg/ml of a surfactant; about 0.01 mg/ml to about 1.0 mg/ml of a chelating agent; and wherein the formulation has a pH at about 5.0 to about 6.0. In some embodiments, the antibody comprises a heavy chain variable region (VH) CDR1 having the amino acid sequence shown in SEQ ID NO: 1, a VH CDR2 having the amino acid sequence shown in SEQ ID NO: 2, a VH CDR3 having the amino acid sequence shown in SEQ ID NO: 3, or a variant of SEQ ID NO: 3, and a light chain variable region (VL) CDR1 having the amino acid sequence shown in SEQ ID NO: 4, a VL CDR2 having the amino acid sequence shown in SEQ ID NO: 5, and a VL CDR3 having the amino acid sequence shown in SEQ ID NO: 6. In some embodiments, the anti-VEGF antibody comprises a VH region comprising the amino acid sequence of SEQ ID NO: 7, and a VL region comprising the amino acid sequence of SEQ ID NO: 8. In some embodiments, the anti-VEGF antibody is AVASTIN® (anti-VEGF antibody or rhuMAb VEGF). In some embodiments, the buffer is succinate buffer, the polyol is sucrose, the surfactant is a polysorbate (e.g., polysorbate 80), and/or the chelating agent is EDTA (or edetate).

In some embodiments, the aqueous formulation of an anti-VEGF antibody drug substance disclosed herein may be stored in sterilized ethylene vinyl acetate (EVA) bags with ethylene vinyl acetate monomaterial (EVAM) product contact surface. In some embodiments, the aqueous formulation of an anti-VEGF antibody drug substance disclosed herein may be stored in a stainless steel container.

According to a further aspect of the present invention, there is provided an aqueous formulation comprising or consisting of: about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, or about 160 mg/ml of an anti-vascular endothelial growth factor (VEGF) antibody (e.g., human anti-VEGF antibody); about 1 mM to about 100 mM of a buffer; about 1 mg/mL to about 300 mg/mL of a polyol; about 0.01 mg/ml to about 10 mg/ml of a surfactant; about 0.01 mg/ml to about 1.0 mg/ml of a chelating agent; and wherein the formulation has a pH at about 5.0 to about 6.0. In some embodiments, the antibody comprises a heavy chain variable region (VH) CDR1 having the amino acid sequence shown in SEQ ID NO: 1, a VH CDR2 having the amino acid sequence shown in SEQ ID NO: 2, a VH CDR3 having the amino acid sequence shown in SEQ ID NO: 3, or a variant of SEQ ID NO: 3, and a light chain variable region (VL) CDR1 having the amino acid sequence shown in SEQ ID NO: 4, a VL CDR2 having the amino acid sequence shown in SEQ ID NO: 5, and a VL CDR3 having the amino acid sequence shown in SEQ ID NO: 6. In some embodiments, the antibody is anti-VEGF antibody (AVASTIN® or rhuMAB VEGF).

In some embodiments, the concentration of the antibody in the formulation is between about 1-150 mg/mL, about 5-145 mg/mL, about 5-80 mg/mL, about 10-140 mg/mL, about 15-135 mg/mL, about 20-130 mg/mL, about 25-125 mg/mL, about 25-50 mg/mL, about 30-120 mg/mL, about 35-115 mg/mL, about 40-110 mg/mL, about 45-105 mg/mL, about 50-100 mg/mL, about 55-95 mg/mL, about 60-90 mg/mL, about 65-85 mg/mL, about 70-80 mg/mL, or about 75 mg/mL. For example, in some embodiments, the concentration of the antibody in the formulation contains less than or equals to about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 70 mg/mL, about 75 mg/mL, about 80 mg/mL, about 90 mg/mL, about 100 mg/mL, about 110 mg/mL, about 120 mg/mL, about 130 mg/mL, about 140 mg/mL, or about 150 mg/mL. In some embodiments, the antibody is anti-VEGF antibody (e.g., AVASTIN® or rhuMAB VEGF) at a concentration of about 25 mg/mL.

According to a further aspect of the present invention there is provided an aqueous formulation comprising or consisting of: about 25 mg/ml to about 150 mg/ml of an anti-vascular endothelial growth factor (VEGF) antibody, or antigen-binding fragment thereof; about 20 mM of a buffer; about 1 mg/mL to about 300 mg/mL of a polyol; about 0.1 mg/ml to about 0.3 mg/ml of a surfactant; about 0.025 mg/ml to about 0.075 mg/ml of a chelating agent; and wherein the formulation has a pH at about 5.0 to about 6.0. In some embodiments, the antibody a heavy chain variable region (VH) CDR1 having the amino acid sequence shown in SEQ ID NO: 1, a VH CDR2 having the amino acid sequence shown in SEQ ID NO: 2, a VH CDR3 having the amino acid sequence shown in SEQ ID NO: 3, or a variant of SEQ ID NO: 3, and a light chain variable region (VL) CDR1 having the amino acid sequence shown in SEQ ID NO: 4, a VL CDR2 having the amino acid sequence shown in SEQ ID NO: 5, and a VL CDR3 having the amino acid sequence shown in SEQ ID NO: 6. In some embodiments, the anti-VEGF antibody comprises a VH region comprising the amino acid sequence of SEQ ID NO: 7, and a VL region comprising the amino acid sequence of SEQ ID NO: 8. In some embodiments, the anti-VEGF antibody is anti-VEGF antibody (AVASTIN® or rhuMAB VEGF). In some embodiments, the buffer is a succinate buffer, the polyol is sucrose, the chelating agent is EDTA (or edetate), and/or the surfactant is polysorbate 80.

In some embodiments, provided is an aqueous formulation comprising or consisting of: about 25 mg/ml or about 150 mg/ml of an antibody that specifically binds to a human anti-vascular endothelial growth factor (VEGF) antibody; about 20 mM of succinate buffer; about 85 mg/mL of sucrose; about 0.2 mg/ml of polysorbate 80; about 0.025 mg/ml to about 0.05 mg/ml of EDTA (or edetate); and wherein the formulation has a pH at about 5.5. In some embodiments, the antibody a heavy chain variable region (VH) CDR1 having the amino acid sequence shown in SEQ ID NO: 1, a VH CDR2 having the amino acid sequence shown in SEQ ID NO: 2, a VH CDR3 having the amino acid sequence shown in SEQ ID NO: 3, or a variant of SEQ ID NO: 3, and a light chain variable region (VL) CDR1 having the amino acid sequence shown in SEQ ID NO: 4, a VL CDR2 having the amino acid sequence shown in SEQ ID NO: 5, and a VL CDR3 having the amino acid sequence shown in SEQ ID NO: 6. In some embodiments, the anti-VEGF antibody is AVASTIN® or rhuMAB VEGF.

In some embodiments, the formulation as described herein has a shelf life of at least or more than about 6 months, 12 months, 18 months, 24 months, 30 months, 36 months, 42 months, or 48 months (e.g., at 5° C., 25° C., or 40° C.). For example, in some embodiments, the formulation of the present invention has a shelf life of at least about 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months, or 60 months (e.g., at 5° C., 25° C., or 40° C.).

In some embodiments, the formulation as described herein has less than about 5% HMMS at 40° C. for up to 1 month, 2 months, 3 months, 4 months, 5 months, or 6 months (e.g., as measured by size exclusion HPLC). In some embodiments, the formulation as described herein has less than about 5% HMMS at 2-8° C. for up to 36 months (e.g., as measured by size exclusion HPLC). In some embodiments, the formulation as described herein has less than about 1% HMMS at 40° C. for up to 1 month, 2 months, 3 months, 4 months, 5 months, or 6 months (e.g., as measured by size exclusion HPLC). In some embodiments, the formulation as described herein has less than about 5% Fragment at 2-8° C. for up to 36 months (e.g., as measured by reducing capillary gel electrophoresis).

Unless stated otherwise, the concentrations listed herein are those concentrations at ambient conditions, i.e., at 25° C. and atmospheric pressure.

Methods of Using the Anti-VEGF Antibody Formulation

The formulations of the present invention are useful in various applications including, but are not limited to, therapeutic treatment methods.

In one aspect, the invention provides a method for for treating diseases and pathological conditions. In particular, the invention provides an effective approach for treating cancers. Accordingly, in some embodiments, provided is a method of treating or inhibiting cancer in a subject in need thereof comprising administering to the subject a therapeutically effective amount of the formulation as described herein. In some embodiments, provided is a use of the formulation of the present invention for the manufacture of a medicament for treatment of cancer.

The cancer amendable for treatment by the present invention include, for example without limitation, carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. In some embodiments, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. In some embodiments, the cancer is colorectal cancer. The cancerous conditions amendable for treatment of the invention include metastatic cancers. The method of the present invention is particularly suitable for the treatment of vascularized tumors.

Any chemotherapeutic agent exhibiting anticancer activity can be used according to the present invention. Preferably, the chemotherapeutic agent is selected from the group consisting of alkylating agents, antimetabolites, folic acid analogs, pyrimidine analogs, purine analogs and related inhibitors, *vinca* alkaloids, epipodopyyllotoxins, antibiotics, L-Asparaginase, topoisomerase inhibitor, interferons, platinum cooridnation complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. More preferably, the chemotherapeutic agent is selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s). Suitable dosing regimens of combination chemotherapies are known in the art and described in, for example, Saltz et al. (1999) Proc ASCO 18:233a and Douillard et al. (2000) Lancet 355:1041-7.

Accordingly, in some embodiments, provided is a method of treating or inhibiting cancer in a subject in need thereof comprising administering to the subject a therapeutically effective amount of the formulation as described herein, wherein the cancer is selected from the group consisting of colorectal cancer, rectal cancer, non-squamous non-small cell lung cancer (NSCLC), non-Hodgkins lymphoma (NHL), metastatic renal cell cancer (mRCC), prostate cancer, liver cancer, pancreatic cancer, soft-tissue sarcoma, kaposi's sarcoma, carcinoid carcinoma, head and neck cancer, melanoma, ovarian cancer, mesothelioma, glioblastoma, cervical cancer, breast cancer, and multiple myeloma. In some embodiments, the cervical cancer is persistent, recurrent, or metastatic cervical cancer. In some embodiments, the colorectal cancer in metastatic colorectal cancer (MCRC)

In some embodiments, the formulation of the present invention can be administered directly into the blood stream, into muscle, into tissue, into fat, or into an internal organ of a subject. Suitable means for parenteral administration include intravenous, intraocular, intravitreal, intraarterial, intraperitoneal, intrathecal, intraventricular, intraurethral, intrasternal, intracranial, intramuscular, intra-ossial, intradermal and subcutaneous. Suitable devices for parenteral administration include needle (including microneedle, microprojections, soluble needles and other micropore formation techniques) injectors, needle-free injectors and infusion techniques. In some embodiments, the formulation of the present invention is administered to the subject intravenously or subcutaneously.

In some embodiments, the administration pattern of the formulation of the present invention comprises administration of a dose of the formulation once every week, once every two weeks, once every three weeks, once every four weeks, once every five weeks, once every six weeks, once every seven weeks, once every eight weeks, once every nine weeks, once every ten weeks, once every fifteen weeks, once every twenty weeks, once every twenty five weeks, or once every twenty six weeks. In some embodiments, the formulation of the present invention is administered once every month, once every two months, once every three months, once every four months, once every five months, or once every six months.

Dosage regimens may depend on the pattern of pharmacokinetic decay that the practitioner wishes to achieve. For example, in some embodiments, dosing from one-four times a week is contemplated. Even less frequent dosing may be used. In some embodiments, the dose is administered once every 1 week, every 2 weeks, every 3 weeks, every 4 weeks, every 5 weeks, every 6 weeks, every 7 weeks, every 8 weeks, every 9 weeks, every 10 weeks, every 15 weeks, every 20 weeks, every 25 weeks, or longer. In some embodiments, the dose is administered once every 1 month, every 2 months, every 3 months, every 4 months, every 5 months, every 6 months, or longer. The progress of this therapy is easily monitored by conventional techniques and assays. The dosing regimen can vary over time.

In some embodiments, the dose of the formulation of the present invention is administered at a dose of 5 mg/kg IV every two weeks. In some embodiments, the dose of the formulation of the present invention is administered at a dose of 10 mg/kg IV every two weeks. In some embodiments, the dose of the formulation of the present invention is administered at a dose of 7.5 mg/kg IV every three weeks. In some embodiments, the dose of the formulation of the present invention is administered at a dose of 7.5 mg/kg IV every three weeks with fluoropyrimidine-irinotecan or fluoropyrimidine-oxaliplatin based chemotherapy after progression on a first-line Avastin® containing regimen. In some embodiments, the dose of the formulation of the present invention is administered at a dose of 15 mg/kg IV every three weeks.

For the purpose of the present invention, the appropriate dosage of the medicament will depend on the antibody employed, the type and severity of the disorder to be treated, whether the agent is administered for preventative or therapeutic purposes, previous therapy, the patient's clinical history and response to the agent, and the discretion of the attending physician. Typically the clinician will administer the medicament, until a dosage is reached that achieves the desired result. Dosages may be determined empirically.

Dose and/or frequency can vary over course of treatment. Empirical considerations, such as the antibody half-life, generally will contribute to the determination of the dosage. Frequency of administration may be determined and adjusted over the course of therapy, and is generally, but not necessarily, based on treatment and/or suppression and/or amelioration and/or delay of one or more symptoms of autoimmune disease. In some individuals, more than one dose may be required. Frequency of administration may be determined and adjusted over the course of therapy. For example without limitation, for repeated administrations over several days or longer, depending on the disease and its severity, the treatment is sustained until a desired suppression of symptoms occurs or until sufficient therapeutic levels are achieved to reduce blood glucose levels.

Administration of the formulation of the present invention can be continuous or intermittent, depending, for example, upon the recipient's physiological condition, whether the purpose of the administration is therapeutic or prophylactic, and other factors known to skilled practitioners. The administration of the formulation of the present invention can be essentially continuous over a preselected period of time or may be in a series of spaced dose.

Preferably the administration of the dose is a parenteral administration preferably selected from intravenous, intraocular, intravitreal, intraarterial, intraperitoneal, intrathecal, intraventricular, intraurethral, intrasternal, intracranial, intramuscular, intra-ossial, intradermal and subcutaneous. Preferably the formulation is in a unit dosage sterile form for parenteral administration (e.g., intravenous administration).

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1. Formulation Development Stability Study of the Succinate-Sucrose-EDTA-Polysorbate 80 (SSEP) Antibody Formulation Containing Anti-VEGF Antibody To evaluate the anti-VEGF antibody formulation of choice, a stability study including anti-VEGF antibody in the SSEP formulation (Table 2A) and anti-VEGF antibody in the commercial formulation (Table 2B) was performed. Anti-VEGF antibody drug substance from a developmental batch was formulated to prepare the anti-VEGF antibody in the SSEP formulation and anti-VEGF antibody in the commercial formulation. The data were also compared with that from the stability study on a representative lot of the anti-VEGF antibody licensed product ("AVASTIN®") to provide a preliminary assessment of the formulations. In this Example, the anti-VEGF antibody used has a heavy chain variable region having the amino acid sequence of SEQ ID NO: 7, and a light chain variable region having the amino acid sequence of SEQ ID NO: 8.

TABLE 2A

SSEP (pH 5.5)

| Name of Ingredients | Unit Formula (mg/mL) |
| --- | --- |
| Anti-VEGF antibody | 25 or 150 |
| Disodium succinate hexahydrate | 4.08 |
| succinic acid | 0.58 |
| Sucrose | 85 |
| Disodium edetate dihydrate (EDTA) | 0.05 |
| Polysorbate 80 | 0.2 |

TABLE 2B

Commercial (pH 6.2)

| Name of Ingredients | Unit Formula (mg/mL) |
| --- | --- |
| Anti-VEGF antibody | 25 or 150 |
| monobasic sodium phosphate (monohydrate) | 5.8 |
| dibasic sodium phosphate (anhydrous) | 1.2 |
| Trehalose (dihydrate) | 60 |
| Polysorbate 20 | 0.4 | pH-buffer screening was conducted to assess the impact of the buffer system and pH in the range of 5.2 to 6.0 on the molecule in the absence of other stabilizing excipients. Development formulation stability studies were conducted to compare anti-VEGF antibody in the commercial formulation (phosphate, pH 6.2) with buffer systems at lower pH values (pH 5.5 and 5.8) to provide optimum drug product stability. Samples were then analyzed for quality attributes that are commonly used to monitor product degradation such as Size-Exclusion HPLC (SE-HPLC). Anti-VEGF antibody was diluted to 25 mg/mL, formulated in either the commercial formulation or the SSEP formulation, filled into glass vials, sealed with fluoropolymer coated stoppers, capped with aluminum seals, and stored upright at 5° C. and 25° C. for a duration of 22 weeks or 40° C. for a duration of 12 weeks.

SE-HPLC results for storage at 25° C. are shown in Table 3 and FIG. 1. As seen in Table 3 and FIG. 1, significantly less degradation was observed in the SSEP formulation compared to commercial formulation after storage of anti-VEGF antibody for 4, 8, 12, and 22 weeks. These results demonstrate anti-VEGF antibody in the SSEP formulation (pH 5.5) is more stable than anti-VEGF antibody in the commercial formulation (pH 6.2) under both real-time and accelerated stability conditions.

TABLE 3

SE-HPLC results for high molecular mass species (% HMMS).

| Antibody formulation | % HMMS | | | | |
| --- | --- | --- | --- | --- | --- |
| | 0 weeks | 4 weeks | 8 weeks | 12 weeks | 22 weeks |
| Anti-VEGF antibody in Succinate, pH 5.5 (SSEP), 25° C. | 1.025 | 1.07 | 0.86 | 0.915 | 1.15 |
| Anti-VEGF antibody in Phosphate, pH 6.2, 25° C. | 2.53 | 3.015 | 2.855 | 2.755 | 3.925 |

Example 2. Formulation Robustness Stability Study of the Succinate-Sucrose-EDTA-Polysorbate 80 (SSEP) Antibody Formulation Containing Anti-VEGF Antibody A formulation robustness stability study of anti-VEGF antibody in the SSEP formulation (target excipients) and anti-VEGF antibody prepared with either high or low excipient levels (±25% range assessed for succinate, sucrose, and EDTA and ±50% range for polysorbate-80) were stored at 5 and 30° C. for a duration of 12 months and 6 months, respectively. Samples were then analyzed using analytical methods selected to monitor biochemical stability. In this Example, the anti-VEGF antibody used has a heavy chain variable region having the amino acid sequence of SEQ ID NO: 7, and a light chain variable region having the amino acid sequence of SEQ ID NO: 8. Results from the most stability indicating method (SE-HPLC) are shown below in Table 4 and FIG. 2.

TABLE 4

SE-HPLC results for high molecular mass species (% HMMS).

| Antibody formulation | % HMMS | | | | |
|---|---|---|---|---|---|
| | 0 months | 1 month | 3 months | 6 months | 12 months |
| Control (Target Excipients), 5° C. | 1.7 | 1.5 | NS | 1.5 | 1.5 |
| High Excipients, 5° C. | 1.6 | 1.4 | NS | 1.4 | 1.4 |
| Low Excipients, 5° C. | 1.7 | 1.5 | NS | 1.5 | 1.5 |
| Control (Target Excipients), 30° C. | 1.7 | 1.5 | 1.7 | 2.0 | NS |
| High Excipients, 30° C. | 1.6 | 1.4 | 1.4 | 1.7 | NS |
| Low Excipients, 30° C. | 1.7 | 1.5 | 1.6 | 1.9 | NS |

Figure 2:
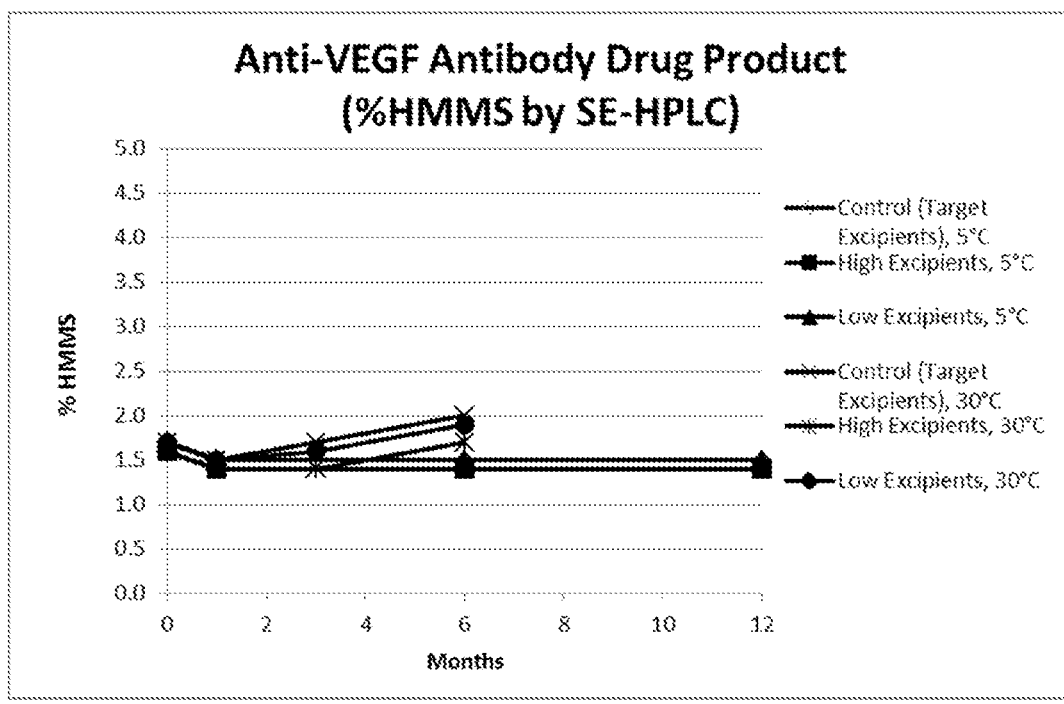
FIG. 2 depicts a graph summarizing the amount of high molecular mass species (% HMMS) for anti-VEGF antibody drug product in either target formulation (SSEP), high excipients, or low excipients and stored at 5° C. and 30° C.

The data shown in Table 4 and FIG. 2 demonstrate that anti-VEGF antibody is stable under both real-time and accelerated stability conditions in the SSEP formulation. Furthermore, samples containing either high excipients or low excipient levels are comparable to samples at the target excipient levels (Control formulation) demonstrating formulation robustness.

Example 3. Forced Degradation Stability Study of Anti-VEGF Antibody in the Succinate-Sucrose-EDTA-Polysorbate 80 (SSEP) Antibody Formulation as Compared to the Commercial Antibody Formulation A subsequent formulation development stability study of anti-VEGF antibody—in the SSEP formulation (5 lots) and anti-VEGF antibody—prepared in the commercial formulation (1 lot in sodium phosphate-trehalose-polysorbate 20, pH 6.2) were assessed at 40° C. for a duration of 12 weeks. Samples were then analyzed for quality attributes that are commonly used to monitor product degradation using SE-HPLC, iCE, and rCGE. In this Example, the anti-VEGF antibody used has a heavy chain variable region having the amino acid sequence of SEQ ID NO: 7, and a light chain variable region having the amino acid sequence of SEQ ID NO: 8. Results are summarized in Tables 5-8 below.

TABLE 5

SE-HPLC results for high molecular mass species (% HMMS).

| Formulation | Antibody | % HMMS | | | | |
|---|---|---|---|---|---|---|
| | | 0 weeks | 4 weeks | 6 weeks | 8 weeks | 12 weeks |
| SSEP | Anti-VEGF antibody-, 40° C. (Lot 13SQ02) in SSEP | 0.8 | 1.4 | 1.8 | 2.3 | 3.4 |
| | Anti-VEGF antibody-, 40° C. (Lot H49500) in SSEP | 0.8 | 1.5 | 1.8 | 2.4 | 3.2 |
| | Anti-VEGF antibody-, 40° C. (Lot H90818-W) in SSEP | 0.7 | 1.2 | 1.7 | 2.0 | 3.1 |
| | Anti-VEGF antibody-, 40° C. (Lot J12512-W) in SSEP | 0.8 | 1.3 | 1.7 | 2.2 | 3.3 |
| | Anti-VEGF antibody-, 40° C. (Lot J12513-W) in SSEP | 0.6 | 1.3 | 1.6 | 2.2 | 3.0 |
| Commercial | Anti-VEGF antibody- in Commercial Formulation, 40° C. (Lot 00706596-0045) | 1.8 | 6.0 | 8.3 | 11.3 | 15.4 |

Significantly less degradation (as measured by % HMMS) was observed in the SSEP formulation compared to commercial formulation after 4, 6, 8, and 12 weeks of storage (Table 5).

TABLE 6

Reducing capillary gel electrophoresis (CGE-reducing) results for fragment (% Fragment).

| Formulation | Antibody | % Fragment | | | | |
|---|---|---|---|---|---|---|
| | | 0 weeks | 4 weeks | 6 weeks | 8 weeks | 12 weeks |
| SSEP | Anti-VEGF antibody-, 40° C. (Lot 13SQ02) in SSEP | 1.2 | 2.5 | 5.3 | 6.2 | 8.6 |
| | Anti-VEGF antibody-, 40° C. (Lot H49500) in SSEP | 0.8 | 2.4 | 5.4 | 6.2 | 7.9 |
| | Anti-VEGF antibody-, 40° C. (Lot H90818-W) in SSEP | 1.1 | 2.3 | 5.2 | 5.9 | 8.1 |
| | Anti-VEGF antibody-, 40° C. (Lot J12512-W) in SSEP | 1.1 | 2.3 | 5.2 | 6.1 | 8.4 |
| | Anti-VEGF antibody-, 40° C. (Lot J12513-W) in SSEP | 0.4 | 2.3 | 5.2 | 5.9 | 7.8 |
| Commercial | Anti-VEGF antibody- in Commercial Formulation, 40° C. (Lot 00706596-0045) | 1.1 | 3.4 | 7.6 | 9.0 | 12.2 |

Less degradation (as measured by % fragment) was observed in the SSEP formulation compared to commercial formulation after 4, 6, 8, and 12 weeks of storage (Table 6).

Tables 7-8 below summarize stability data for anti-VEGF mAb-SSEP (anti-VEGF antibody in SSEP formulation) and anti-VEGF mAb-commercial (anti-VEGF antibody in commercial formulation) after storage for 1 month at 40° C. Stability tables show change from T=0. In Tables 7-8, a=lower amount of HMMS observed in anti-VEGF mAb-lots due to SSEP formulation; b=percent difference calculated for cell-based assay. CGE=Capillary Gel Electrophoresis, iCE=imaged Capillary Electrophoresis, HMMS=High Molecular Mass Species. In this Example, the anti-VEGF antibodies used have a heavy chain variable region having the amino acid sequence of SEQ ID NO: 7, and a light chain variable region having the amino acid sequence of SEQ ID NO: 8.

TABLE 7

| Analytical Procedure | Evaluation Parameter | Anti-VEGF mAb-SSEP, 400 mg Lot # 13SQ02 | Anti-VEGF mAb-SSEP, 400 mg Lot # H49500 | Anti-VEGF mAb-SSEP, 400 mg Lot # H90818-W |
|---|---|---|---|---|
| iCE | Acidic Peaks (%) | +28.5 | +25.9 | +29.4 |
| | Main Peak (%) | −29.7 | −25.3 | −31.7 |
| | Basic Peaks (%) | +1.2 | −0.5 | +2.3 |
| Size Exclusion HPLC | Monomer (%) | −2.5 | −2.6 | −2.6 |
| | HMMS (%)$^a$ | +0.6 | +0.7 | +0.5 |
| CGE (reducing) | Heavy Chain + Light Chain (%) | −1.2 | −1.7 | −1.2 |
| | Fragment (%) | +1.3 | +1.6 | +1.2 |
| | Other (%) | −0.2 | +0.2 | −0.1 |
| Cell-based assay | Relative Potency (%)$^b$ | −11% | −5% | 0% |
| HIAC (Particles per mL) | ≥2 μm | −177 | −112 | −346 |
| | ≥5 μm | −43 | −31 | −91 |
| | ≥8 μm | −14 | −9 | −28 |
| | ≥10 μm | −6 | −2 | −9 |
| | ≥25 μm | 0 | 0 | 0 |

TABLE 8

| Analytical Procedure | Evaluation Parameter | Anti-VEGF mAb-SSEP, 100 mg Lot # J12512-W | Anti-VEGF mAb-SSEP, 100 mg Lot # J12513-W | Anti-VEGF mAb-, Commercial Formulation, Lot 00706596-0045 |
|---|---|---|---|---|
| iCE | Acidic Peaks (%) | +28.2 | +26.3 | +27.3 |
| | Main Peak (%) | −30.0 | −25.8 | −26.0 |
| | Basic Peaks (%) | +1.8 | −0.5 | −1.3 |
| Size Exclusion HPLC | Monomer (%) | −2.5 | −2.4 | −6.2 |
| | HMMS (%)$^a$ | +0.5 | +0.7 | +4.2 |
| CGE (reducing) | Heavy Chain + Light Chain (%) | −1.3 | −2.1 | −2.4 |
| | Fragment (%) | +1.2 | +1.9 | +2.3 |
| | Other (%) | +0.1 | +0.2 | +0.1 |
| Cell-based assay | Relative Potency (%)$^b$ | +2% | +1% | −20% |
| HIAC (Particles per mL) | ≥2 μm | −199 | +330 | −66 |
| | ≥5 μm | −45 | +18 | −24 |
| | ≥8 μm | −16 | −8 | −11 |
| | ≥10 μm | −8 | −7 | −8 |
| | ≥25 μm | −1 | −1 | −2 |

These results demonstrate that the SSEP formulation provides increased anti-VEGF antibody drug product stability compared to the commercial formulation. The data demonstrate that the anti-VEGF antibody product (anti-VEGF mAb-) is more stable in the SSEP formulation as compared to the commercial formulation in that upon storage at elevated temperatures, there was less HMMS and fragment formed.

Example 4. Long-Term Stability Study of the Succinate-Sucrose-EDTA-Polysorbate 80 (SSEP) Antibody Formulation Containing Anti-VEGF Antibody to Establish Drug Substance and Drug Product Shelf-Life A subsequent stability study of anti-VEGF antibody—in the SSEP formulation was set up at lab-scale to establish the shelf-life of the drug substance and drug product.

Anti-VEGF antibody drug substance (Lot 00706253-007) at 120 mg/mL was stored in sterilized ethylene vinyl acetate (EVA) bags with ethylene vinyl acetate monomaterial (EVAM) product contact surface for 36 months at −20° C. (recommended storage) and −40° C. (back-up/alternate temperature) and 3 months at 5° C. The samples were assessed by the following analytical methods: Appearance (clarity, coloration, visual), pH, UV-Spectroscopy, iCE, SE-HPLC, CGE (non-reducing), and cell-based assay. Supportive stability data up to 36 months for samples stored at −20° C. and −40° C. show no significant differences when compared to the initial data. At 3 months, development samples stored at 5° C. show no significant differences when compared to initial data. In this Example, the anti-VEGF antibody used has a heavy chain variable region having the amino acid sequence of SEQ ID NO: 7, and a light chain variable region having the amino acid sequence of SEQ ID NO: 8. Results from the most stability indicating method (SE-HPLC) are shown below in Table 9.

TABLE 9

SE-HPLC results for high molecular mass species (% HMMS).

| Sample Information | % HMMS as a Function of Time (Months) | | | | | | | | | |
|---|---|---|---|---|---|---|---|---|---|---|
| | 0 | 1 | 2 | 3 | 6 | 9 | 12 | 18 | 24 | 36 |
| Lot 00706253-007, −20 C. | 0.81 | 0.87 | 1.2 | 0.9 | 1.2 | 1.29 | 1.0 | 1.0 | 1 | 1.05 |
| Lot 00706253-007, −40 C. | 0.81 | NS | NS | 0.9 | 1.2 | 1.27 | 1 | NS | 0.9 | 0.99 |
| Lot 00706253-007, 5 C. | 0.81 | 0.92 | NS | 1.0 | NS | NS | NS | NS | NS | NS |

NS = Not Scheduled.

Anti-VEGF antibody drug product (Lot 00706596-003) at 25 mg/mL was stored inverted in glass vials that were sealed with fluoropolymer coated stoppers and capped with aluminum seals for 36 months at 5° C. and 12 months at 25° C. The samples were assessed by the same analytical methods as used for drug substance with an additional low-volume HIAC method for sub-visible particulate matter analysis. Supportive stability data up to 36 months for samples stored at 5° C. show no significant differences when compared to the initial data. At 3 months, development samples stored at 25° C. show no significant differences when compared to initial data. Results from the most stability indicating method (SE-HPLC) are shown below in Table 10.

TABLE 10

SE-HPLC results for high molecular mass species (% HMMS).

| Sample Information | % HMMS as a Function of Time (Months) | | | | | | | | | |
|---|---|---|---|---|---|---|---|---|---|---|
| | 0 | 1 | 2 | 3 | 6 | 9 | 12 | 18 | 24 | 36 |
| Anti-VEGF antibody-, 5° C. (Lot 00706596-0003) | 0.9 | 0.8 | 0.7 | 0.7 | 0.9 | 1.0 | 0.8 | 0.8 | 0.9 | 0.9 |
| Anti-VEGF antibody-, 25° C. (Lot 00706596-0003) | 0.9 | 1.1 | 0.9 | 0.8 | 1.2 | 1.6 | 1.4 | NS | NS | NS |

NS = Not Scheduled.

The results from this study of anti-VEGF antibody in the SSEP formulation have been used to establish a shelf-life of at least 36 months at −20° C. or −40° C. for drug substance at 120 mg/mL and at least 36 months at 5° C. for drug product at 25 mg/mL.

Example 5. Stability Study of Histidine-Sucrose-EDTA-Polysorbate 80 (HSEP) Aqueous Formulation Containing Anti-VEGF Antibody This example illustrates anti-VEGF antibody drug product stability in an HSEP formulation.

An HSEP aqueous formulation was designed for anti-VEGF antibody at a concentration of approximately 25 mg/mL. Specifically, a HSEP formulation used in this example included 8.5% sucrose, 0.05 mg/mL EDTA, 0.02% Polysorbate 80 in 20 mM histidine at pH 5.5. The protein concentration was assessed at 25 and 100 mg/mL (for anti-VEGF antibody-).

Anti-VEGF antibody was prepared in 20 mM histidine (pH 5.5 and 5.8) and 20 mM succinate (pH 5.5 and 5.8) with constant amounts of 8.5% sucrose, 0.05 mg/mL EDTA, 0.02% Polysorbate 80 and compared to anti-VEGF antibody in the commercial formulation (phosphate, trehalose, polysorbate 20, pH 6.2). Drug substance (100 mg/mL) was stored in EVA bags for 8 weeks at −40° C., −20° C., and 5° C. and drug product (25 mg/mL) was stored in Type I glass vials for 22 weeks at 2-8° C. and 25° C. and 12 weeks at 40° C. In this Example, the anti-VEGF antibody used has a heavy chain variable region having the amino acid sequence of SEQ ID NO: 7, and a light chain variable region having the amino acid sequence of SEQ ID NO: 8. The SE-HPLC Data for % HMMS after storage of anti-VEGF antibody drug product (25 mg/mL) at 40° C. is summarized below in Table 11.

TABLE 11

| Drug Product (at 40° C.) | % HMMS Time (weeks) | | | | |
|---|---|---|---|---|---|
| | 0 | 2 | 4 | 8 | 12 |
| anti-VEGF antibody in Histidine 5.5 DP | 1.4 | 1.5 | 1.9 | 2.3 | 3.4 |
| anti-VEGF antibody in Histidine 5.8 DP | 2.1 | 2.7 | 3.1 | 3.9 | 5.6 |
| anti-VEGF antibody in Succinate 5.5 DP | 1.0 | 1.3 | 1.7 | 1.8 | 2.4 |
| anti-VEGF antibody in Succinate 5.8 DP | 1.2 | 2.1 | 2.5 | 2.5 | 3.9 |
| anti-VEGF antibody in Phosphate 6.2 DP | 2.5 | 8.1 | 9.2 | 10.6 | 13.0 |

Figure 3:
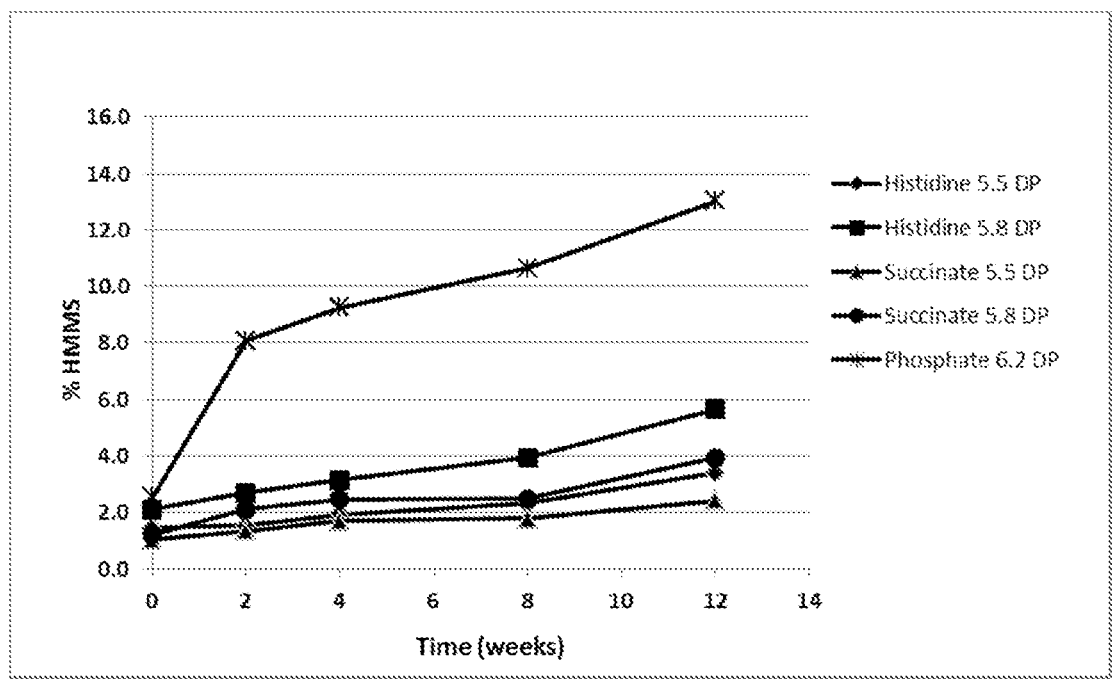
FIG. 3 depicts a graph summarizing the amount of high molecular mass species (% HMMS) by SE-HPLC for anti-VEGF antibody in histidine, succinate, or phosphate formulations at 40° C.

The data shows a significant increase in % HMMS for anti-VEGF antibody in the commercial formulation (phosphate, pH 6.2) (Table 11 and FIG. 3). The succinate and histidine-based formulations have a much lower rate of HMMS formation, with the Succinate-pH 5.5 as the optimal formulation followed by Histidine-pH 5.5, Succinate-pH 5.8 and Histidine-pH 5.8, respectively.

These results demonstrate that anti-VEGF antibody is significantly more stable in succinate and histidine-based formulations having pH 5.5 or 5.8 than in the commercial formulation.

The invention claimed is:

1. An aqueous formulation comprising:
   about 25 mg/ml of an anti-vascular endothelial growth factor (VEGF) antibody;
   about 20 mM histidine or succinate buffer;
   about 85 mg/mL sucrose;
   about 0.2 mg/ml polysorbate 80;
   about 0.05 mg/ml EDTA;
   wherein the antibody comprises a heavy chain variable region comprising the amino acid sequence of SEQ ID NO: 7, and a light chain variable region comprising the amino acid sequence of SEQ ID NO: 8; and
   wherein the formulation has pH at about 5.5 or 5.8.

2. The aqueous formulation of claim 1, wherein the formulation comprises histidine buffer.

3. The aqueous formulation of claim 1, wherein the formulation comprises succinate buffer.

4. The aqueous formulation of claim 1, wherein the formulation has pH at about 5.5.

5. The aqueous formulation of claim 1, wherein the formulation has pH at about 5.8.

* * * * *